US011366280B1

(12) United States Patent
Courter, Jr.

(10) Patent No.: US 11,366,280 B1
(45) Date of Patent: Jun. 21, 2022

(54) LENS MOUNT APPARATUS AND METHOD

(71) Applicant: Lawrence Leroy Courter, Jr., Costa Mesa, CA (US)

(72) Inventor: Lawrence Leroy Courter, Jr., Costa Mesa, CA (US)

( * ) Notice: Subject to any disclaimer, the term of this patent is extended or adjusted under 35 U.S.C. 154(b) by 0 days.

(21) Appl. No.: 17/157,628

(22) Filed: Jan. 25, 2021

Related U.S. Application Data

(63) Continuation of application No. 16/740,231, filed on Jan. 10, 2020, now Pat. No. 10,901,167, which is a continuation-in-part of application No. 16/240,717, filed on Jan. 5, 2019, now abandoned, which is a continuation of application No. 14/872,854, filed on Oct. 1, 2015, now Pat. No. 10,175,446.

(51) Int. Cl.
| | |
|---|---|
| *G02B 17/00* | (2006.01) |
| *G02B 7/02* | (2021.01) |
| *G02B 1/04* | (2006.01) |
| *B29C 45/56* | (2006.01) |
| *B29C 45/16* | (2006.01) |
| *A61F 9/02* | (2006.01) |
| *B29L 11/00* | (2006.01) |

(52) U.S. Cl.
CPC ............. *G02B 7/021* (2013.01); *B29C 45/16* (2013.01); *B29C 45/561* (2013.01); *G02B 1/041* (2013.01); *A61F 9/025* (2013.01); *B29L 2011/0016* (2013.01)

(58) Field of Classification Search
CPC ........ G02B 7/021; G02B 1/041; B29C 45/16; B29C 45/561; B29L 2011/0016; A61F 9/025
See application file for complete search history.

(56) References Cited

U.S. PATENT DOCUMENTS

| | | |
|---|---|---|
| 5,555,038 A | 9/1996 | Conway |
| 5,790,230 A | 8/1998 | Sved |
| 6,170,952 B1 | 1/2001 | La Haye et al. |
| 6,502,937 B2 | 1/2003 | Yang |
| 7,641,333 B2 | 1/2010 | Blanshay et al. |
| 7,648,233 B2 | 1/2010 | Blanshay et al. |
| 8,025,395 B2 | 9/2011 | Quintana |
| 8,083,344 B2 | 12/2011 | Blanshay et al. |
| 8,104,890 B2 | 1/2012 | Blanshay et al. |
| 8,814,349 B2 | 8/2014 | Goebel Quintana |
| 10,444,533 B2 | 10/2019 | Lussier et al. |
| 10,901,167 B1 * | 1/2021 | Courier, Jr. ............ G02B 7/021 |
| 2007/0252942 A1 | 11/2007 | Collier |
| 2012/0140162 A1 | 6/2012 | Chen |
| 2015/0131047 A1 | 5/2015 | Saylor |

* cited by examiner

*Primary Examiner* — James C. Jones
(74) *Attorney, Agent, or Firm* — Master Key IP, LLP; Jeromye V. Sartain

(57) ABSTRACT

A lens mount apparatus comprising a first lens component and a second lens component joined integrally with the first lens component, resulting in mechanochemical attachment of the second lens component with the first lens component to produce the unitary lens mount apparatus without compromising the lens mount apparatus optics, wherein at least one of the first and second lens components is an optical lens.

20 Claims, 7 Drawing Sheets

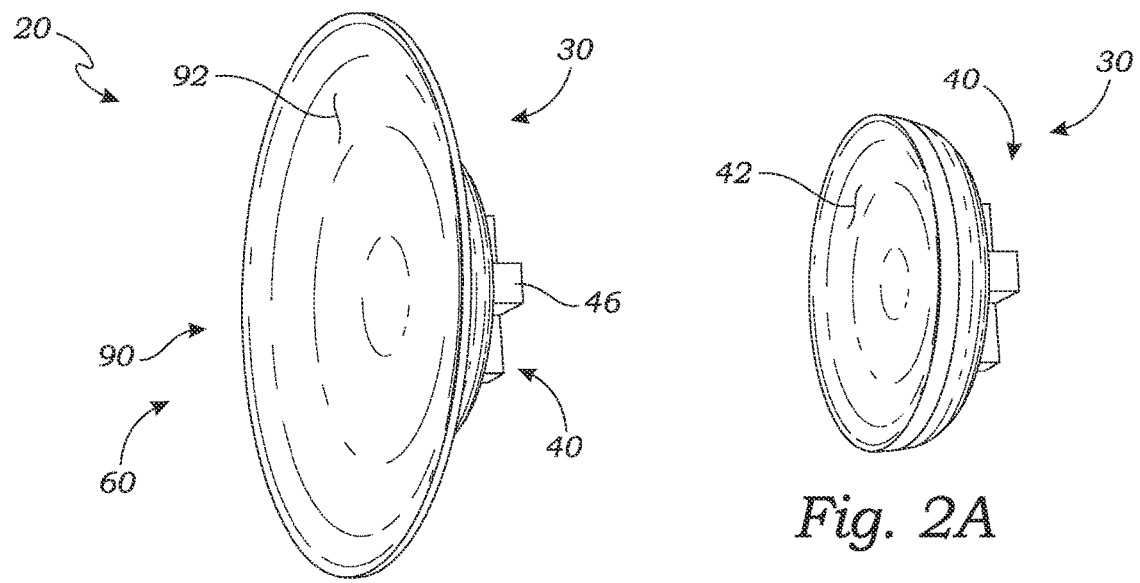
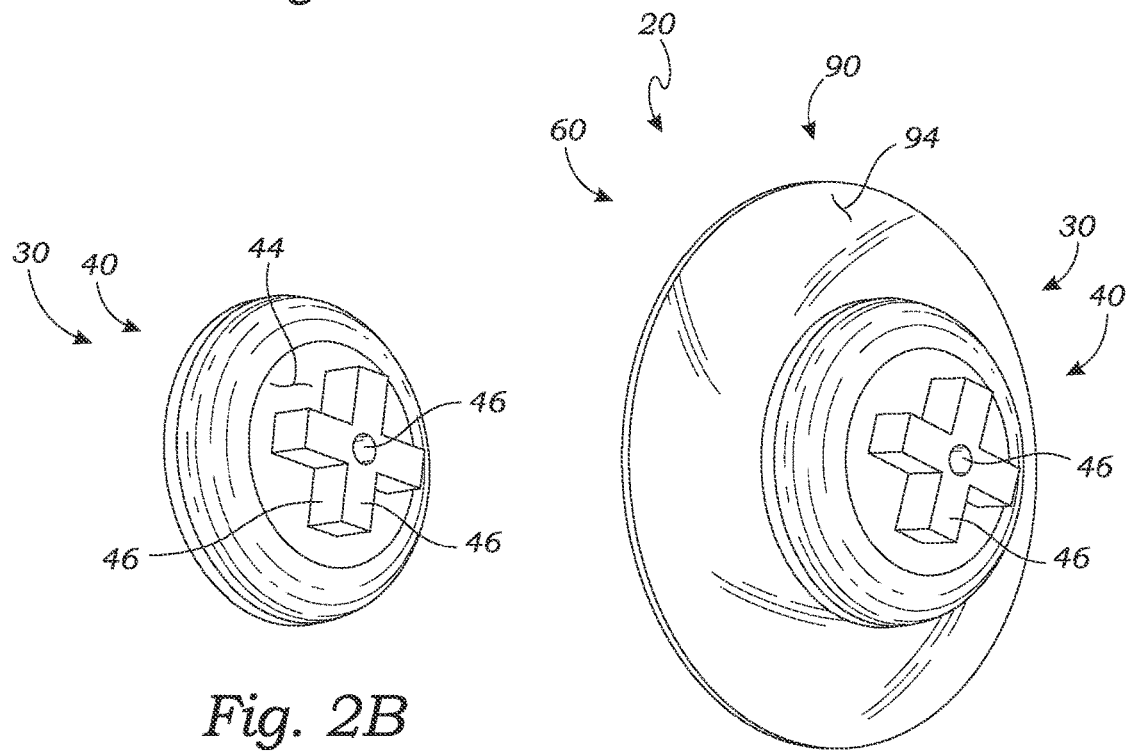

LENS MOUNT APPARATUS AND METHOD

RELATED APPLICATIONS

This is a continuation application and so claims the benefit pursuant to 35 U.S.C. § 120 of a prior filed and co-pending U.S. Non-Provisional patent application Ser. No. 16/740,231 filed Jan. 10, 2020, and entitled "Lens Mount Apparatus and Method," which itself is a continuation-in-part application and so claims the benefit pursuant to 35 U.S.C. § 120 of a prior filed U.S. Non-Provisional patent application Ser. No. 16/240,717 filed Jan. 5, 2019, and entitled "Lens Mount Apparatus and Method," which itself is a continuation application and so claims the benefit pursuant to 35 U.S.C. § 120 of a prior filed U.S. Non-Provisional patent application Ser. No. 14/872,854 filed Oct. 1, 2015, and entitled "Lens Mount Apparatus and Method," now U.S. Pat. No. 10,175,446 issued Jan. 8, 2019. The contents of the aforementioned applications are incorporated herein by reference.

BACKGROUND

The subject of this patent application relates generally to structures and manufacturing techniques for lenses and lens assemblies and/or related mounting supports, and more particularly to lens mount apparatuses and methods configured for producing lens assemblies with or without integral mounting supports yet without compromising the lens optics.

Applicant(s) hereby incorporate herein by reference any and all patents and published patent applications cited or referred to in this application.

By way of background, lenses are generally classified by the curvature of the two (front and back) optical surfaces, each of which are typically spherical, or made up of a part of the surface of a sphere. A lens is biconvex if both surfaces are convex, biconcave if both surfaces are concave, or concave-convex or meniscus if one surface is convex and the other surface is concave. If one of the surfaces is flat, the lens is plano-convex or plano-concave depending on the curvature of the surface of the lens opposite the flat surface. The most common type of lens in ophthalmology or for use as a "corrective" or "prescription" lens is essentially a positive meniscus. Other kinds of specialized lenses include toric or sphero-cylindrical lenses and aspheric lenses, having one or more non-spherical surfaces, cylindrical lenses, Fresnal lenses, lenticular lenses, gradient index lenses, axicons, and superlenses.

The process of forming finished lenses of virtually any shape or configuration has traditionally been accomplished through a glass lens blank manufacturing process or essentially a casting process wherein a glass powder is melted and poured into the lens blank cavity and then annealed. More recently, with the advent and improved technology of thermoplastic materials such as polycarbonate, injection molding of lens blanks has become the preferred method of producing many kinds of lenses, including ophthalmic or corrective or prescription lenses. In either case—glass or plastic—where corrective lenses are to be formed, the "prescription" curvature is cut or ground into the lens blank to produce the finished lens with the desired optical properties. The challenge in both initially forming the lens blank and then in cutting into the blank the desired curvature to form the finished lens is to not introduce distortion or stress into the lens that would adversely affect its optical qualities.

As is known, finished lenses in the case of traditional ophthalmic use are then mounted in frames or support structure of some kind so as to be worn for effective optical performance, such as vision correction in the case of traditional eyewear with nose and ear pieces. In this application, the lenses are effectively snapped into position within eyewear frames, such as within inwardly-opening retention grooves of the frame designed to match the perimeter or profile of the lens, or the lens cut to match the frame profile, or the lenses are otherwise mounted or secured by screwing or fastening a retaining member to the main part of the frame so as to clamp the lens in place. Even lenses in other contexts such as telescopes or microscopes must be mounted or held in the desired position for the passage of light therethrough or the reflection of light thereof. Oftentimes, corrective lenses are incorporated into or used in conjunction with further lenses, whether for additional optical properties or to provide a protection or safety function or both, such as in protective helmets, hoods, face shields, visors and the like, including for military or ballistic applications, or simply as part of eyewear for sports or other recreational use such as sunglasses and goggles. Other contexts for lenses in this modern age relate to "virtual reality" headsets, "heads up" displays, and the like. In virtually all such contexts, it is desirable to not just produce but be able mount the lens within a support structure whereby the lens may be held and positioned where needed without causing any distortion or otherwise adversely affecting the optical properties of the lens. Further, it is desirable irrespective of how any such lens or lens assembly will be mounted to be able to produce unitary lens assemblies even including or incorporating prescription lenses or lens blanks, again without adversely affecting the optical properties of the finished lens or lens assembly and even without adversely affecting the ballistic or impact protection properties of the lens or lens assembly.

In short, the variety and increasing complexity of lens applications and the attendant challenges of properly manufacturing and mounting such lenses has resulted in needs that have heretofore gone unmet in the industry.

As further background, U.S. Patent Application Publication No. 2015/0131047 entitled "Eyewear with Laminated Functional Layers" is directed to eyewear that has one or more laminates applied to a lens body. In some embodiments, the lens body is constructed from a substantially rigid material having a curved shape. The lens body can have any desired curvature, including, for example, cylindrical, spherical or toroidal. A laminate can include a substantially flexible substrate and one or more functional layers or coatings applied to the substrate. In addition, one or more functional layers or coatings can be applied directly to the lens body. In certain embodiments, a bonding layer bonds a laminate to a convex and/or concave surface of the lens body. Examples of functional layers or coatings that can be applied to a laminate include anti-reflection coatings, interference stacks, hard coatings, flash mirrors, anti-static coatings, anti-fog coatings, other functional layers, or a combination of functional layers.

U.S. Patent Application Publication No. 2012/0140162 entitled "Glasses Construction" is directed to a glasses construction including an auxiliary frame coupled with optical lenses and disposed as needed behind the middle portion of a glasses frame coupled with lenses, and a protective frame disposed behind and snap-engaged with the glasses frame. The glasses frame and the protective frame together limit the position of the auxiliary frame. Two connecting elements pivotally disposed on two sides of the glasses frame, respectively, are snap-engaged with connecting members extending from the ends of two temples and stopping portions formed beside the connecting members to thereby form a glasses construction. Hence, the combination or separation between the glasses frame and the protective frame, between the glasses frame and the auxiliary frame, or between two said connecting elements pivotally disposed on two sides of the glasses frame and the temples is advantageously characterized by quick positioning or removal by convenient operation.

U.S. Patent Application Publication No. 2007/0252942 entitled "Eyewear with Inner and Outer Frame and Lens" is directed to eyewear that includes an outer frame having a right temple arm and a left temple arm. An outer lens is secured to the outer frame. An inner frame is removably secured to the outer frame. An inner lens is positioned in the inner frame. A portion of the outer lens engages the inner frame to removably secure the inner frame to the outer frame.

U.S. Pat. No. 8,814,349 entitled "One-Piece Lens with Surplus Inner Optical Material" is directed to a one-piece lens made from optical material that includes an outside part and an inside part, in which the inside parts comprise a surplus amount of the same optical material as the lens, for the purpose of cutting ophthalmic lenses, the surplus material being positioned close to the central part of the lens. While there is thus provided at least some teaching of a unitary lens construction having an inner prescription lens portion and a relatively larger outer lens portion, no provision is made for integrating or forming the lens from multiple components or with any mounting supports, much less doing so without compromising the lens optics.

U.S. Pat. No. 8,025,395 entitled "Industrial Safety Goggles with Frame for Ophthalmic Micas and Impact Protection Mica" is directed to industrial safety goggles provided with permanent ophthalmic micas having a full impact protection mica positioned thereon, wherein the impact protection mica is made from polycarbonate, providing protection against ultraviolet rays and can be removed, thereby enabling the frames to be used as ophthalmic glasses. The goggles include a ventilation area and the ophthalmic micas have an improved visual field owing to the design of the frame to which they are mounted and fixed using angular incisions in the frame. The frame is provided with an open space at both eyes between the mica and the end of the rim, which provides ventilation and prevents the fogging of the graduated micas.

U.S. Pat. No. 7,641,333 entitled "Protective Eyewear Including Auxiliary Lenses" is directed to an eyewear assembly including an outer first frame, at least one outer first lens, an inner second frame, and at least one inner second lens. The assembly includes a mechanism for holding the first frame and first lens in front of a user's face. The second frame has a mechanism for attachment to the first frame, to hold the second frame between the user's eyes and the first lens. The at least one second lens is carried by the second frame. The second frame includes a first frame portion that mounts the second lens and a second frame portion over-molded onto the first frame portion defining portions of the outside surface area of the second frame. The first frame portion is of a relatively hard material and the second frame portion is of a relatively soft material. A shock-absorbing pad can be fit between the first and second frames.

U.S. Pat. No. 6,502,937 entitled "Eyewear with Prescription Lens Inserts" is directed to eyewear comprising an eyewear frame, at least one lens in the eyewear frame, and an attachment device for holding a prescription lens insert so that the prescription lens insert is held in position adjacent the lens of the eyewear thereby to correct the vision of a wearer of the eyewear.

U.S. Pat. No. 6,170,952 entitled "Adherent Corrective Lenses and Eyeglasses Embodying the Same" is directed to a magnifying and/or corrective lens or optical element that may be removably adhered to a plano lens, such as the pane of a pair of spectacles or sunglasses, without the use of a mechanical retention device or other mechanical means for retention. The lenses are injection-molded from an aliphatic thermoplastic polyurethane, and capable of conforming to a variety of surface shapes and of adhering via tactile interactions to a plano lens without the use of an adhesive. The lenses may be securely but releasably secured to the surface of a plano lens by finger pressure alone due to their inherent molecular surface-adhesion characteristics to readily create magnifying or corrective lenses, or to modify the magnification or correction of a pair of sunglasses or plano eyeglasses. The lens of the present invention has at least one curved surface and a refractive index such that the curved surface and the refractive index cooperatively produce a nominal magnifying power. The present invention is also directed to a pair of spectacles that comprise a magnifying and/or corrective lens securely adhered to a pane of a pair of spectacles without the use of a mechanical retention device.

Once more, the art neither discloses nor suggests lens mount apparatuses and methods configured for producing lenses or lens assemblies with or without integral mounting supports yet without compromising the lens optics as by inducing stresses or distortion in the lens. Aspects of the present invention fulfill these needs and provide further related advantages as described in the following summary.

SUMMARY

Aspects of the present invention teach certain benefits in construction and use which give rise to the exemplary advantages described below.

The present invention solves the problems described above by providing a lens mount apparatus. In at least one embodiment, the lens mount apparatus comprises a first lens component and a second lens component formed integrally with the first lens component, resulting in mechanochemical attachment of the second lens component with the first lens component to produce the unitary lens mount apparatus without compromising the lens mount apparatus optics, wherein at least one of the first and second lens components is an optical lens.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings:

FIG. 1 is a perspective view of an exemplary lens mount apparatus, in accordance with at least one embodiment;

FIG. 2A is a perspective view of a first lens component thereof, in accordance with at least one embodiment;

FIG. 2B is a rear perspective view thereof, in accordance with at least one embodiment;

FIG. 3 is a rear perspective view of the lens mount apparatus of FIG. 1, in accordance with at least one embodiment;

Figure 4:
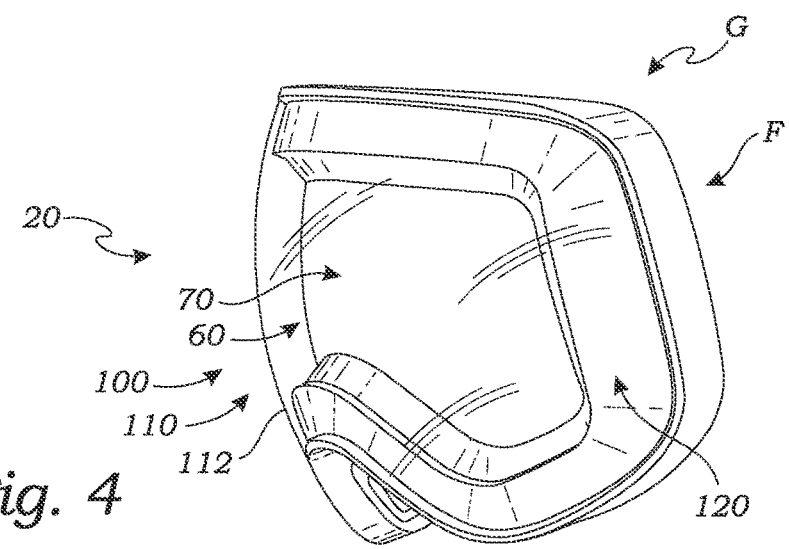
FIG. 4 is a side perspective view of an alternative exemplary lens mount apparatus incorporated within a goggle, in accordance with at least one embodiment.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

DETAILED DESCRIPTION

As a threshold matter, it is noted that when the word "lens" or the phrase "optical lens" is used herein, any optical member, or component having defined optical qualities, is intended to be included, whether such lens is transparent or clear, translucent or tinted, opaque, or reflective or mirrored, or any combination thereof, and whether with respect to light passing in one direction, both directions, or any direction through the lens or reflecting off of the lens, so long as the lens has certain designed and intended optical properties for transmitting or reflecting light in a desired fashion to suit a particular optics application, such that distortion in the lens is to be avoided as potentially or actually adversely affecting the optical performance of the lens. Any such lens as contemplated herein may be made of any material and be of any geometry or thickness to suit any application, whether now known or later developed. Accordingly, "lens" as used throughout is to be understood as having a broader meaning than its typical or standard definition and to include or encompass, again, any component having defined or intended optical qualities or functioning as an optical device.

Referring now to FIG. 1, there is shown a perspective view of an exemplary embodiment of a lens mount apparatus 20. The apparatus 20 comprises, in the exemplary embodiment, a first lens component 30 and a second lens component 60 formed integrally with the first lens component 30. As shown, the second lens component 60 defines a second perimeter that is greater than the first perimeter defined by the first lens component 30, though it will be appreciated that this is not necessarily the case—that in alternative embodiments the first and second perimeters may be substantially equal or the first perimeter may be greater than the second perimeter. At a high level, it is noted that in the illustrated embodiment of the lens mount apparatus 20 the first lens component 30 is configured as a lens support device 40 having one or more mechanical attachment features 46 for subsequently mounting the integrated second lens component 60 that is here configured as a meniscus second optical lens 90 having a concave outer surface 92 and a convex inner surface 94 (FIG. 3) to which the lens support device 40 is attached. It will be appreciated that in such a configuration with the lens support device 40 mounted substantially centrally on the back of the lens 90 that the lens is here configured as having a mirrored or reflective outer surface 92, though not necessarily. It will also be appreciated that throughout the present specification the terms "outer," "front" or "forward" are used interchangeably to describe features or surfaces that are facing or exposed to one direction, such as toward a light source (not shown), and the terms "inner," "back," "inward," or "rear" or "rearward" are used interchangeably to describe features or surfaces that are facing or exposed to a substantially opposite direction, as with the two opposed sides or surfaces of the lens 90. While in theory the first and second lens components 30, 60 may be formed integrally as shown in FIG. 1 as by being molded or otherwise formed in a single "shot," this is not desirable when, as here, one or more of the lens components is to be an optical lens, wherein avoiding sinks, stresses, defects, or other issues within the material that cause distortion and thus would adversely affect the designed or intended optical properties of the particular lens component is desired. However, molding or forming the first and second lens components 30, 60 successively one on the other as through over-molding or injection-compression molding or simply molding or forming them separately and then bonding, ultrasonically welding, or otherwise fastening them together would also result in an integral assembly as shown without necessarily compromising the optical properties of the finished lens mount apparatus 20. Advantageously, according to aspects of an exemplary embodiment of the present invention, both the first and second lens components 30, 60 are molded in succession, with the second lens component 60 specifically formed integrally with the first lens component 30 through injection-compression molding the second lens component 60 on the first lens component 30 in a secondary operation, resulting in mechanochemical attachment of the second lens component 60 on the first lens component 30 to produce the unitary lens mount apparatus 20 without compromising the lens mount apparatus optics. Optionally, of course, the second lens component 60 may be formed first and the first lens component 30 formed thereon. Either way, the result is uniform wall thickness components, and particularly the second lens mount component 60 formed as the optical lens 90, having no distortion and thus preserving the intended optical qualities of the lens 90.

Turning now to FIGS. 2A and 2B, there are shown front and rear perspective views of the first lens component 30, again here configured as a lens support device 40. As best seen in FIG. 2A, the lens support device 40 is formed having an outer surface 42 that is substantially concave and thus configured to seat flush with the convex rear or inner surface 94 of the lens 90, best seen in FIG. 3. As illustrated and best seen in FIG. 2B, the rear or inner surface 44 of the lens support device 40 is formed having one or more mechanical attachment features 46 formed thereon or therein. Specifically, shown are both a central hole, which it will be appreciated with reference to FIG. 2A does not pass through the lens support device 40 to the front or outer surface 42 but may be configured with a straight bore of a desired depth to accept a dowel or the like (not shown) as through a press-fit, bonding, or any other such attachment means now known or later developed or may have a threaded bore so as to receive a screw, bolt, or other such threaded fastener now known or later developed. Furthermore, as illustrated, the exemplary mechanical attachment features 46 further comprise a raised, indexing surface that may be keyed to further support structure so as to positively align or prevent the rotation of the lens mount apparatus 20, and the optical lens 90 portion particularly, once in a desired position. It will be appreciated by those skilled in the art that the lens support device 40 and its related mechanical attachment features 46 may take on virtually any form as appropriate for a particular context, such that the exemplary embodiment of FIGS. 1-3 is to be understood as merely illustrative and non-limiting. With continued reference to FIGS. 2A and 2B, the first lens component 30 here configured as the lens support device 40 may be formed through any manufacturing method and employing any appropriate material now known or later developed. Those skilled in the art will appreciate that such a component, if to be plastic, may be formed through an injection or compression-injection molding process as now known or later developed—that all features as shown and described can easily and conventionally be formed through a molding process in a single "shot." According to aspects of the present invention, the first lens component 30 or lens support device 40 may be formed of polycarbonate, though it will be appreciated that any thermoplastic or other material now known or later developed may be employed.

Referring next to FIG. 3, once the first lens component 30 or lens support device 40 as shown in FIGS. 2A and 2B is formed as by molding, in a secondary operation the second lens component 60 here configured as an optical lens 90 is compression-injection molded directly onto the first lens component 30 to form the lens mount apparatus 20. In a bit more detail, the first lens component 30 may remain in the very same mold cavity and by operation of a slide or otherwise the cavity modified to accommodate a second injection and immediate compression to form and substantially simultaneously effectively fuse the second lens component 60 onto the first lens component 30. Alternatively, the molded first lens component 30 may be placed into an appropriate cavity in a different mold in order to then injection-compression mold the second lens component 60 thereto. In either case, the molded first component 30 may still be warm or may be allowed to cool prior to the second operation of molding the second lens component 60 onto the first lens component 30. It will be appreciated that in either scenario the one or more mechanical attachment features 46 may also serve to index and hold in place the lens support device 40, or first lens component 30, as the second lens component 60 is compression-injection molded thereon. Once more, in the exemplary embodiment, this union to form the integral lens mount apparatus 20 happens between the convex inner surface 94 of the second lens component 60 and the concave outer surface 42 of the first lens component 30. Those skilled in the art will appreciate that the resulting mechanochemical attachment between the first and second lens components 30, 60 is a product of the coupling of mechanical and chemical phenomena on a molecular scale and includes complex transformations induced by pressure and heat, though distinct from usual thermal or photochemical mechanisms. The result is a synthesized or one-piece substantially stress- and distortion-free lens mount apparatus 20 comprising an optically correct polycarbonate lens or mirror surface with no defects or sink marks while having a unitary mounting or fastening structure on the back or other surface of the lens. Again, while the illustrated embodiment entails a symmetrical or round meniscus lens with a substantially centered rear mounting feature that is itself symmetrical, those skilled in the art will appreciate that a virtually infinite variety of lens mount apparatuses according to aspects of the present invention are possible without departing from its spirit and scope.

Turning now to FIGS. 4-8 there is illustrated a further exemplary lens mount apparatus 20 according to aspects of the present invention, here in the context of eyewear and essentially an ophthalmological application. Particularly, as shown in the side perspective view of FIG. 4, the alternative lens mount apparatus 20 is advantageously incorporated into a pair of goggles G, which is particularly beneficial where corrective or prescription lenses are to be installed or formed within the lens mount apparatus 20 as shown and described in connection with the exemplary embodiment of FIGS. 5 and 6. Generally speaking, the finished goggle G includes its own frame F, with the lens mount apparatus 20 here including effectively a third lens component 100 configured as the outermost shield or front lens 110 of the goggle G, more about which is said below, particularly in connection with the exploded perspective view of FIG. 8 and then the further alternative exemplary embodiment of FIGS. 9-13.

Figure 5:
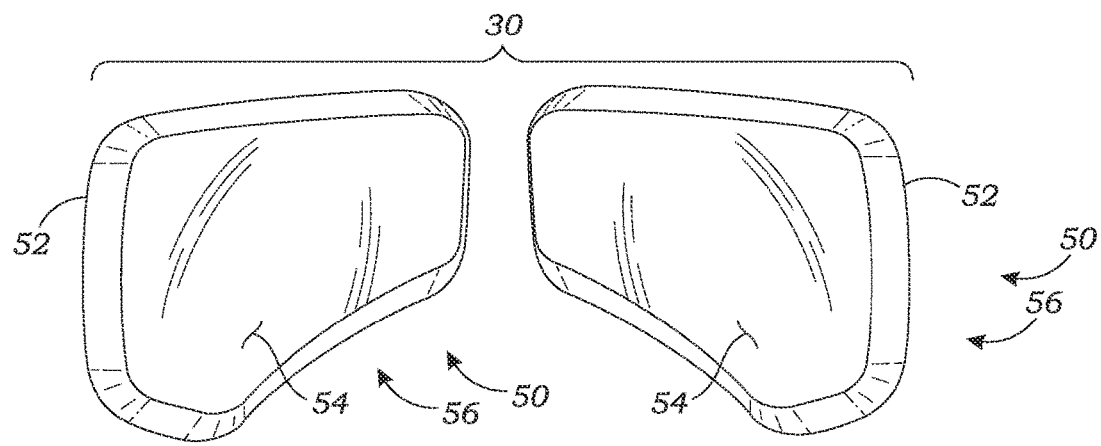
FIG. 5 is a rear perspective view of a first lens component thereof, in accordance with at least one embodiment.

Referring to FIG. 5, there is shown a rear perspective view of the first lens component 30 here as first optical lenses 50 configured as a pair of lens inserts 56. The lens inserts 56 are shown as being essentially mirror images of one another, as essentially left and right lenses 50. The lens inserts 56 may again be formed from any appropriate manufacturing method and material now known or later developed. In the exemplary embodiment the inserts 56 are injection or compression-injection molded from clear polycarbonate. These lens inserts 56 may be formed of virtually any size and shape to suit any particular finished eyewear context, here they being sized and shaped to be narrower toward the middle or the bridge of the nose area when worn and wider toward the temples again when worn so as to have a somewhat trapezoidal shape. The thickness of the lens inserts 56 is a function of both the finished eyewear geometry and the specifications for cutting or grinding the appropriate curvature into the lenses to satisfy what has been prescribed for correction of the wearer's vision. Each lens insert 56 generally has a meniscus curvature, again meaning that the lens outer surface 52 is convex and the lens inner surface 54 is concave, which is typical for corrective or prescription lenses in finished form. As shown, the perimeter of each lens insert may be beveled to assist removal from the mold. It will be appreciated that at this stage the polycarbonate lens inserts 56 form or define lens blanks that may be subsequently machined or cut to a particular curvature in the nature of prescription or corrective lenses. Accordingly, the optical quality of the lens inserts 56 in terms of being free of voids, sinks, stresses, or any other defects must be maintained to render the inserts 56 useful in fashioning prescription lenses. Were the lenses 50 to be mounted in conventional eyewear frames they may then be simply sent to the optometrist or the like for grinding to suit a particular patient and then installed in the selected eyewear frames. However, even in that scenario, the installation of the lenses after they have been ground can induce stresses that adversely affect the lens optics. As such, it would still be preferable to have the frame or mounting features formed integrally with the lenses 50 and in so doing not induce any stresses or distortion in accordance with aspects of the present invention so that after the prescription curvature is ground into the lenses 50, since they already have the necessary frame or at least mounting features formed integrally with the lenses, completion of the eyewear is as simple as attaching other frame features such as the temple pieces. In the exemplary goggle context, the idea is much the same—to incorporate a second lens component 60 formed as a second lens support device 70 integrally on the first lens component 30 here formed as optical or prescription lenses 50 so as to form a lens sub-assembly that can then be installed within the goggle G.

Figure 6:
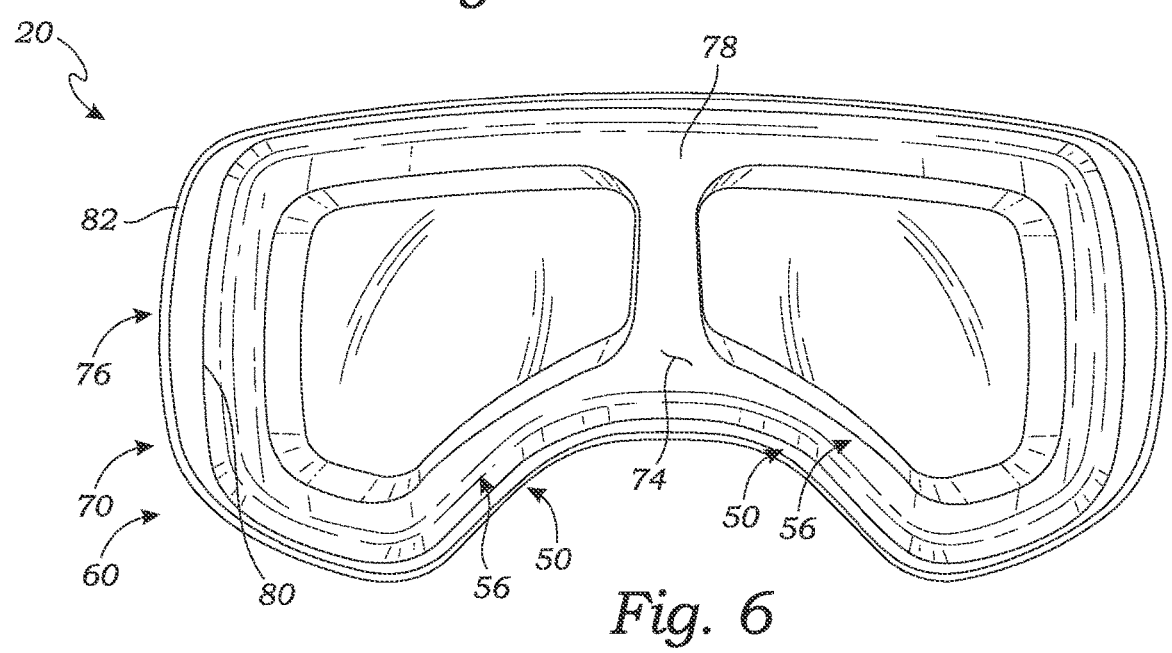
FIG. 6 is a rear perspective view of the lens mount apparatus thereof, in accordance with at least one embodiment.

Turning to FIG. 6, then, there is now shown a rear perspective view of the lens mount apparatus 20 wherein the second lens component 60 in the form of a lens support device 70 is formed integrally on the first lens component 30 in the form of the first optical lenses 50 defining a pair of lens inserts 56 as by compression-injection molding the second lens component 60 on the first lens component 30 (i.e., forming the lens support device 70 on or over the lens inserts 56). As noted in connection with the embodiment of FIGS. 1-3, the compression-injection molding of the second lens component 60 may be in the same mold in which the lens inserts 56 are molded or may be in a separate mold having a cavity to accommodate the inserts 56 in the desired relative positions, and may be with the inserts 56 still warm or cooled first, or the second lens component 60 may be formed first and then the first lens component 30, here in the form of the first optical lenses 50 or the lens inserts 56 specifically, formed subsequently onto the second lens component 60. In either case, the first lens component 30 in the form of the lens inserts 56 and the second lens component 60 in the form of the lens support device 70 are formed so as to essentially fuse the pair of lens inserts 56 to the rear or inner surface 74 thereof as shown. Particularly, it will be appreciated that the somewhat concave curvature of the inner surface 74 of the lens support device 70 substantially conforms to the somewhat convex lens outer surface 52. In the exemplary embodiment, the lens support device 70 is also formed of clear polycarbonate, resulting in a one-piece, monolithic or homogeneous lens sub-assembly having the desired optical quality of no induced stresses, sinks, or other defects, such that as noted above, when a prescription curvature is subsequently ground into the rear or inner surfaces 54 of the lenses 50, or lens blanks 56, no defects or sinks or other issues are encountered and the desired optical properties are achieved, with the resulting prescription sub-assembly then ready for installation into a finished eyewear such as the goggle G (FIG. 4). Notably, the lens support device 70 also then functions as a second optical lens 90 (FIG. 7), with the resulting lens sub-assembly essentially comprising a "shield" or "near net-shape" lens for which no perimeter cutting or shaping would be necessary, as distinct from lens blanks that are to be machined to the desired final shape, thereby reducing the amount of material used and scrapped. It will be appreciated that such a lens sub-assembly or lens mount apparatus 20 may be configured so as to then be attached in final form to an eyewear frame with appropriate attachment means, versus the attachment means shown and described herein as incorporated into the lens support device 70 for the purpose of later assembling the lens mount apparatus 20 within a pair of goggles G (FIG. 4). Accordingly, in the exemplary embodiment, the lens support device 70 is defined by a front or outer lens wall 78 that covers the inner prescription lenses 50. The lens wall 78 further defines a lens wall perimeter 80 having a perimeter flange 82 that extends substantially inwardly. In the exemplary embodiment, in forming the lens support device 70, the at least one mechanical attachment feature 76 is configured in the form of the lens perimeter flange 82. It will be appreciated that the perimeter flange 82 may itself be formed with further attachment features such as notches or holes as required or desired. The shape and depth of the perimeter flange 82 may also vary depending on a number of factors related to the final eyewear configuration as well as the material and manufacturing method selected. Again, a variety of other such attachment features 76 and the configuration of the perimeter flange 82 itself, if included at all, may be incorporated in a lens mount apparatus 20 according to aspects of the present invention without departing from its spirit and scope, such as to suit other eyewear applications.

Figure 7:
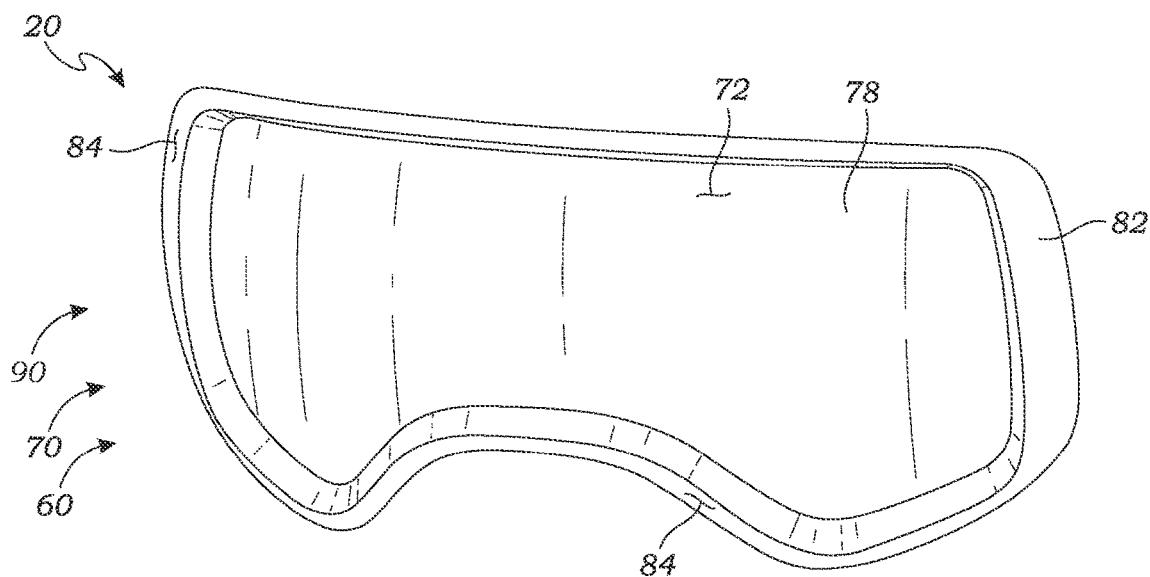
FIG. 7 is a front perspective view thereof, in accordance with at least one embodiment.

Turning briefly to FIG. 7, there is shown a front perspective view of the exemplary lens mount apparatus 20 of FIGS. 4-6. The second lens component 60 is again configured as a lens support device 70 comprising a lens wall 78 that defines the outer surface 72 of the support device 70, which is also effectively configured as a second optical lens 90 contributing to the overall optics of the lens sub-assembly along with the first optical lenses 50 configured as prescription lens blanks or inserts 56. Further, about the perimeter of the lens wall 78 there is formed a perimeter flange 82 that as now seen from the front not only extends inwardly or rearwardly but also outwardly or forwardly of the lens wall 78 so as to form or define an outwardly-facing perimeter flange surface 84 offset outwardly of the support device outer surface 72, more about which is said below in connection with FIG. 8. Those skilled in the art will again appreciate that the overall shape of the lens support device 70 and thus the perimeter flange 82 is merely illustrative and that a variety of other configurations are possible without departing from the spirit and scope of the invention.

Figure 8:
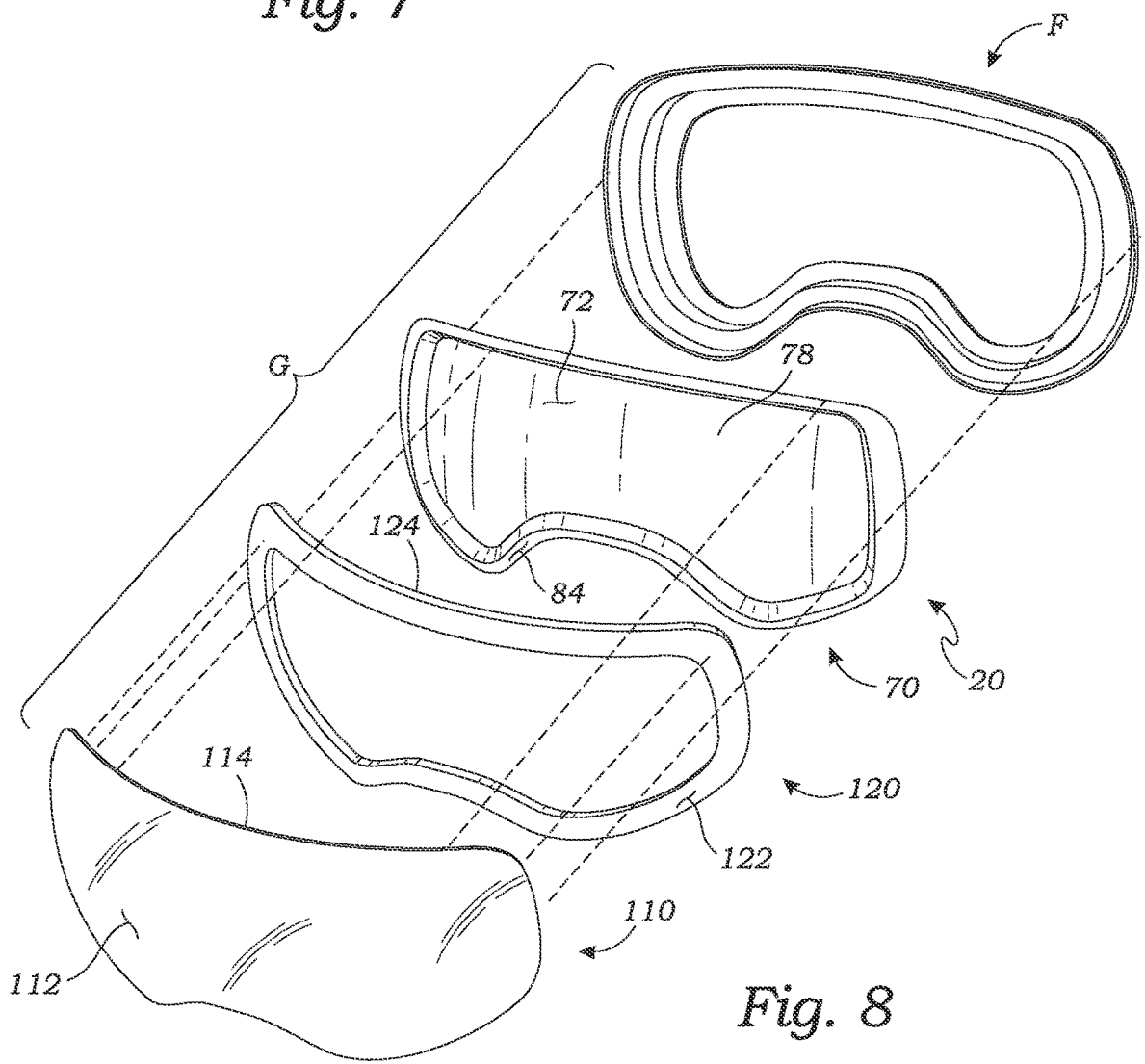
FIG. 8 is an exploded front perspective view thereof, in accordance with at least one embodiment.

With reference now to FIG. 8, there is shown a reduced scale exploded perspective view illustrating the assembly of the lens mount apparatus 20 within a goggle G (FIG. 4). As illustrated, the profiles of the respective components making up the goggle G assembly are substantially the same so that a proper nesting of the components in the finished device is achieved, as shown in FIG. 4. It is particularly noted that in the exemplary embodiment there is included a gasket 120 positioned between the lens mount apparatus 20 and the outer third optical lens 110. More particularly, the perimeter of the gasket 120 is configured to substantially conform to that of both the lens mount apparatus 20 and the outer third optical lens 110, with the inner surface 124 of the gasket configured to substantially seat on and conform to the outwardly-facing perimeter flange surface 84 of the lens mount device 70 and the outer surface 122 of the gasket 120 configured to substantially seat on the third lens inner surface 114 substantially about its perimeter, thereby effectively securing the third lens 110 on the lens mount apparatus 20. As such, the gasket 120 may be formed of a double-sided adhesive foam or the like for forming such assembly, though of course any other material and method of its attachment now known or later developed is possible. In an alternative embodiment there may be no gasket 120 at all, with instead the outer third lens 110 directly seated or installed on the lens mount apparatus 20. In either case, it will be appreciated that due to the stand-off of the perimeter flange 82 (FIG. 7) from the lens wall 78, there is effectively formed a space or air gap between the support device or lens wall outer surface 72 and the inner surface 114 of the outer third lens 110, which air gap aids in the anti-fogging properties of the lens assembly. Moreover, where the gasket 120 is employed, it will be appreciated that a relatively larger stand-off or space between the support device or lens wall outer surface 72 and the inner surface 114 of the outer third lens 110 is achieved, creating an even larger air gap for anti-fogging functionality. Relatedly, by forming the gasket 120 of an open cell foam that allows for a degree of air exchange between the atmosphere and the bound air gap region of the goggle G between the lens mount apparatus 20 and the front or outer lens 110 further anti-fogging performance is achieved along with an insulation effect. That is, an air exchange or pressure regulation functionality is provided without compromising the anti-fogging and insulation properties of the goggles G. While a particular form or geometrical configuration of the goggle G and particularly the gasket 120 are shown, those skilled in the art will appreciate that the assembly may take a number of other forms without departing from the spirit and scope of the invention. Relatedly, it is possible that the grinding of the prescription curvature on the lens inserts 56 (FIGS. 5 and 6) may take place before or after the front lens 120 is assembled on the lens mount apparatus 20 or even after such sub-assembly is installed within the goggle frame F to complete the assembly of the goggles G. The lens mount apparatus 20 may be installed within the frame F employing any attachment technique or feature now known or later developed, and whether permanent or temporary.

Figure 9:
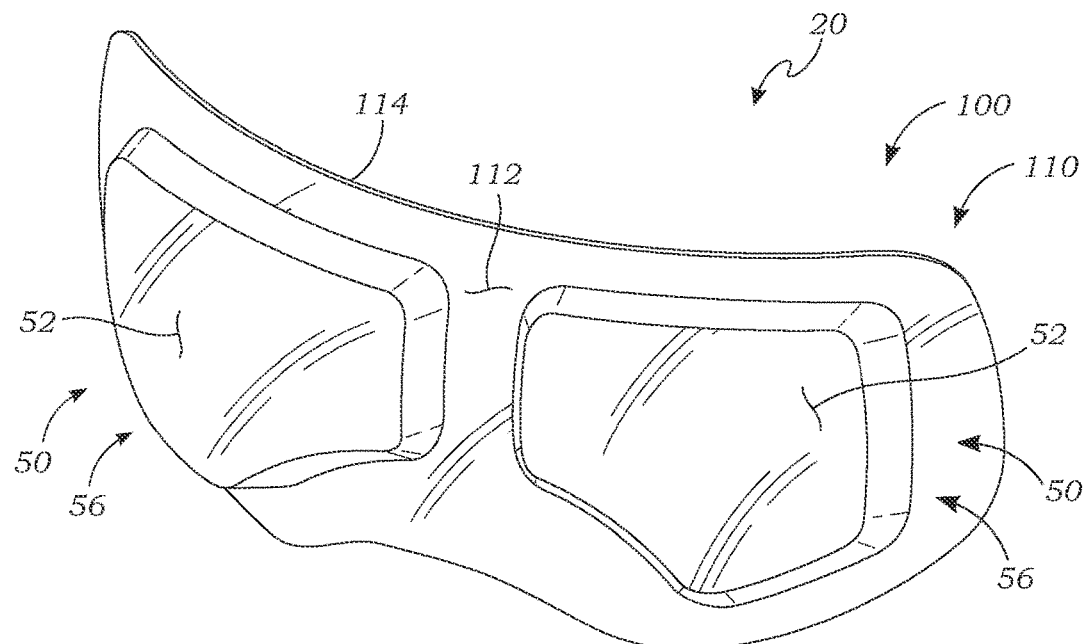
FIG. 9 is a perspective view of a further alternative exemplary lens mount apparatus, in accordance with at least one embodiment.
Figure 10:
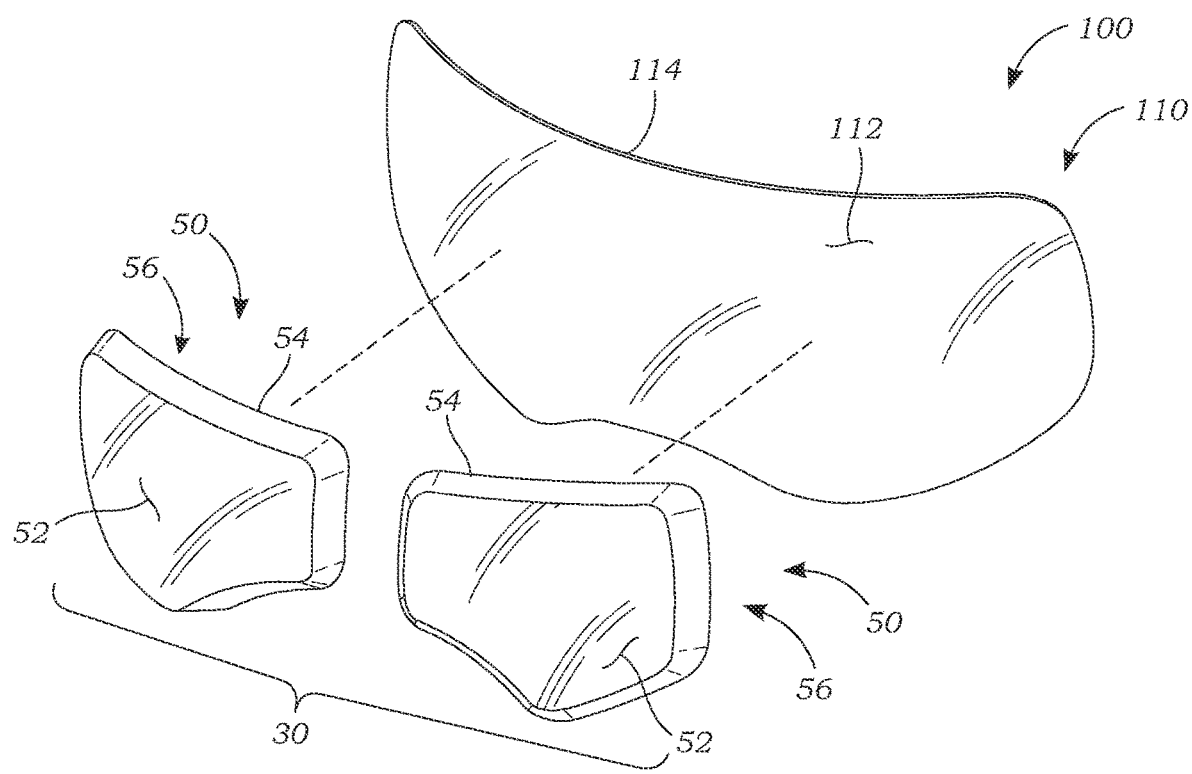
FIG. 10 is an exploded front perspective view thereof, in accordance with at least one embodiment.

Referring next to FIGS. 9-13, there are illustrated further exemplary embodiments of a lens mount apparatus 20 according to aspects of the present invention, here again in the context of eyewear and essentially an ophthalmological application. Specifically, the first lens component 30 is again shown as a pair of prescription lens inserts 56 that are mirror images of one another, as essentially left and right lenses 50, and which may again be formed from any appropriate manufacturing method and material now known or later developed and with the prescription cut, ground, shaped, or otherwise formed in the lenses 50 before, during, or after such are integrally formed or installed on the second or third lens component 60, 100 to form the lens assembly or lens mount apparatus 20. As illustrated in FIGS. 9 and 10, the prescription lenses 50 are formed or affixed onto a unitary shield-type lens component 100, specifically the outer surface 112 of the shield or optical lens 110. However, it will be appreciated by those skilled in the art that the prescription lenses 50 may also be formed or bonded or otherwise integrally affixed onto the inner surface 114 of such an outer shield or third optical lens 110 or onto the outer surface 72 of a second lens support device 70 (or outer surface 92 of a second optical lens 90) (FIGS. 1-3 and 15), in either case the prescription lenses 50 being positioned between the second and third lenses 60, 100, or within the air gap therebetween, as in the case of goggles G (FIGS. 4 and 8) (or where a third lens component 100 is employed, otherwise simply on the outside of the second lens component 60), or the prescription lenses 50 may be formed or bonded onto the inner surface 74 of the second lens support device 70 (or inner surface 94 of the second optical lens 90) as shown in the exemplary embodiment of FIGS. 4-8, and particularly FIG. 6, and whether in any such exemplary embodiments such inner and outer surfaces are concave or convex or are flat or planar, with the lenses 50 and their tapered or beveled edges shaped accordingly, as well as to suit any other related context or commercial application. Those skilled in the art will appreciate that by placing the prescription lenses 50 on the outer surface 92, 72 of any second lens 90 or support 70 or on either the front or back surface 112, 114 of any outermost third lens 110, or basically in any location other than the inside surface 94, 74 of the second lens 90 or support 70, the prescription lenses 50 are thus spaced further from the wearer's eyes and separated therefrom by one or more continuous lens, thereby improving impact resistance in military ballistic or other such eyewear impact testing, or further protecting the wearer's eyes. In any such context, each prescription lens 50 is integrally and permanently installed on any such shield or other lens 90, 110 or support structure 70, and whether on the outer or inner surface thereof, employing any appropriate assembly means now known or later developed, including but not limited to over-molding or injection-compression molding, ultrasonic welding, bonding, including UV light cured solvent and other agents, or additive manufacturing techniques such as stereolithography ("SLA"), selective laser sintering ("SLS"), vacuum deposition, and 3-D printing, more about which is said below. Accordingly, and in any such context of installing, assembling, or otherwise joining any such lens components it will be appreciated that "permanent" or "permanently" or "integral" or "integrally" mean that such parts can only be separated by destruction or that their assembly is irreversible—that once joined they are incapable of nondestructive separation. Relatedly, it will be further appreciated in connection with all exemplary embodiments that the "first," "second," and "third" nomenclature is employed simply to distinguish one lens component (optical lens or lens support device) from another and that such terms are expressly not to be understood as necessarily describing or limiting the location of any such lens components within the finished apparatus or assembly, in terms of position relative to the wearer (closest to or furthest from), or the order in which any such lens components are formed or added to the finished apparatus or assembly. That is, and as consistent with the other exemplary embodiments herein, the first lens component may be formed first and then the second or subsequent lens component formed or assembled thereto, or the second or subsequent lens component may be formed first and then the first lens component formed or assembled thereto, such that once more any such element names are to be understood as non-limiting and simply for ease of reference or labeling. Relatedly and expressly, in connection with the exemplary embodiments of FIGS. 9-13, it will be appreciated that effectively the "first" lens component 30 as the prescription lenses 50 is joined there with the "third" lens component 100 as the shield-type lens 110 to form the complete lens assembly or lens mount apparatus 20, with there not being a "second" lens component 70. Accordingly, when "first" and "second" lens components are recited in the appended claims, it will be appreciated that such terminology is employed interchangeably and is non-limiting other than by the further recited structure, such that, for example, reciting a "first lens component" as prescription lenses and a "second lens component" as a shield-type lens would encompass all such embodiments hereof, including those of FIGS. 4-8 and of FIGS. 9-13. In any such case, the resulting lens assembly or lens mount apparatus 20 may then be installed in any appropriate eyewear device or frame (not shown) without departing from the spirit and scope of the invention.

Figure 11:
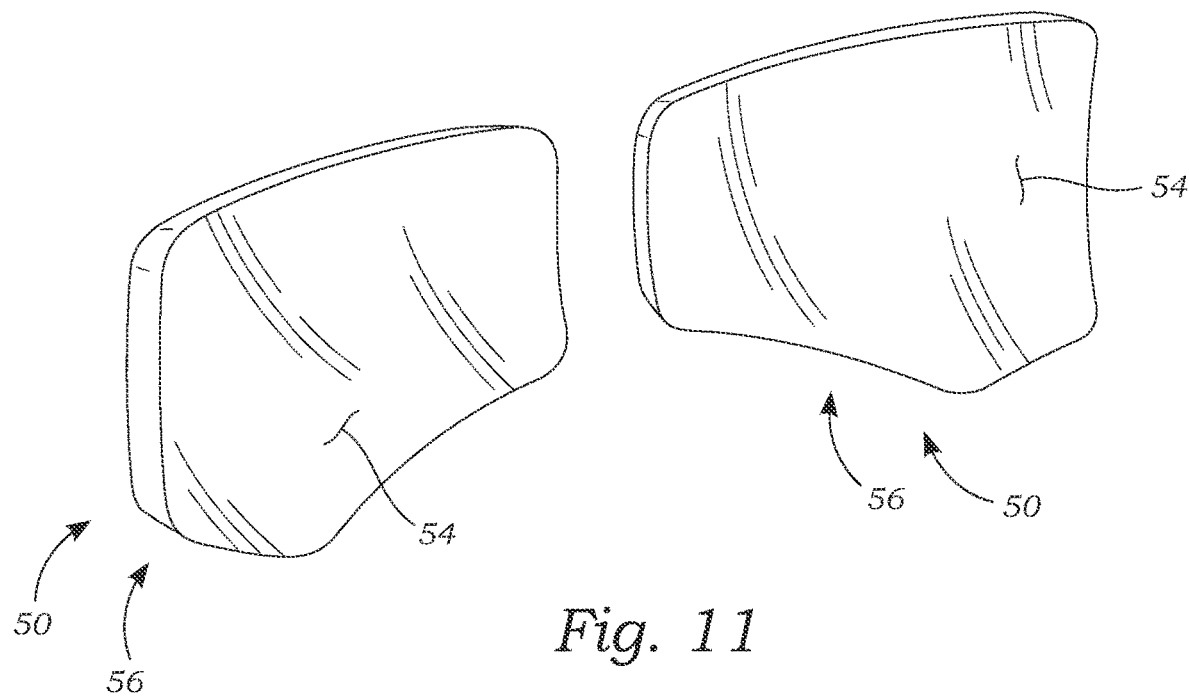
FIG. 11 is a rear perspective view of a first lens component thereof, in accordance with at least one embodiment.

With continued reference to FIGS. 9-11, in a first alternative exemplary embodiment, the prescription lenses 50 or lens inserts 56 and the shield lens 110 are formed separately as through a molding or other such process, whether now known or later developed, and then bonded, affixed, or otherwise assembled together in a secondary operation, more about which is said below. Accordingly, it will be appreciated in the context of prescription lenses 50 that the required prescription or curvature may thus be formed in the lens inserts 56 prior to assembly of the lenses 50 with the shield lens 110, which may in some contexts be more efficient or convenient than grinding or cutting the prescription curvature or shape into the lens inserts 56 after their installation on the shield lens 110, which could create challenges in both fixturing and potential introduction of stress into the lens assembly 20. Once more, the prescription lenses 50 or lens inserts 56 are shown as each formed having a concave inner surface 54 that substantially conforms to the convex outer surface 112 of the shield lens 110. Accordingly, a net or near-net surface-to-surface union is accomplished. Again, though, those skilled in the art will appreciate that where the prescription lenses 50 are to be assembled onto an inner surface 114 of such a shield lens 110, it would be the curvature or shape of each lens outer surface 52 that would substantially conform to the curvature or shape of the shield inner surface 114, which would also follow for assembly onto an outer or inner surface 92, 94 of a second optical lens 90 (FIGS. 1-3 and 15). In the exemplary embodiment, both the shield lens 110 and the prescription lenses 50 are formed of clear polycarbonate, resulting in a one-piece, monolithic or homogeneous lens sub-assembly having the desired optical quality of no induced stresses, sinks, or other defects, such that as noted above, when a prescription curvature is subsequently ground here into the front or outer surfaces 52 of the lenses 50, or lens inserts or blanks 56, if not already done pre-assembly, no defects or sinks or other issues are encountered and the desired optical properties are achieved, with the resulting prescription sub-assembly then ready for installation into a finished eyewear such as a shield or sunglasses frame (not shown) or a goggle G (FIGS. 4 and 8). That is, it will be appreciated that such prescription lenses 50 may be formed on the outer surface 112 of the outermost third shield lens 110 as shown in FIG. 9 and the resulting sub-assembly then be installed directly into a frame or the like for wearing, or effectively the same would be accomplished by forming the lenses 50 on the outer surface 72 of the second lens support device 70, which also functions as the second optical lens 90, and not employing a third outermost lens 90, such that any such shield lens 90, 110 with integral prescription lenses 50 would then be mounted and worn accordingly, versus employing both the inner and outer shield lenses 90, 110 in a goggle G (FIGS. 4 and 8) or the like, with the prescription lenses 50 formed on either such shield lens 90, 110 in various optional configurations. Once again, in any such case, the resulting lens sub-assembly essentially comprises a "shield" or "near net-shape" lens for which no perimeter cutting or shaping would be necessary, as distinct from lens blanks that are to be machined to the desired final shape to suit a particular eyewear frame, thereby reducing the amount of material used and scrapped. It will be appreciated that such a lens sub-assembly or lens mount apparatus 20 may be configured so as to then be attached in final form to an eyewear frame with appropriate attachment means, versus the attachment means shown and described herein as incorporated into one of the shield lenses 90, 110 so as to define a support structure, such as the second lens support device 70 for the purpose of later assembling the lens mount apparatus 20 within a pair of goggles G (FIGS. 4 and 8).

Figure 12:
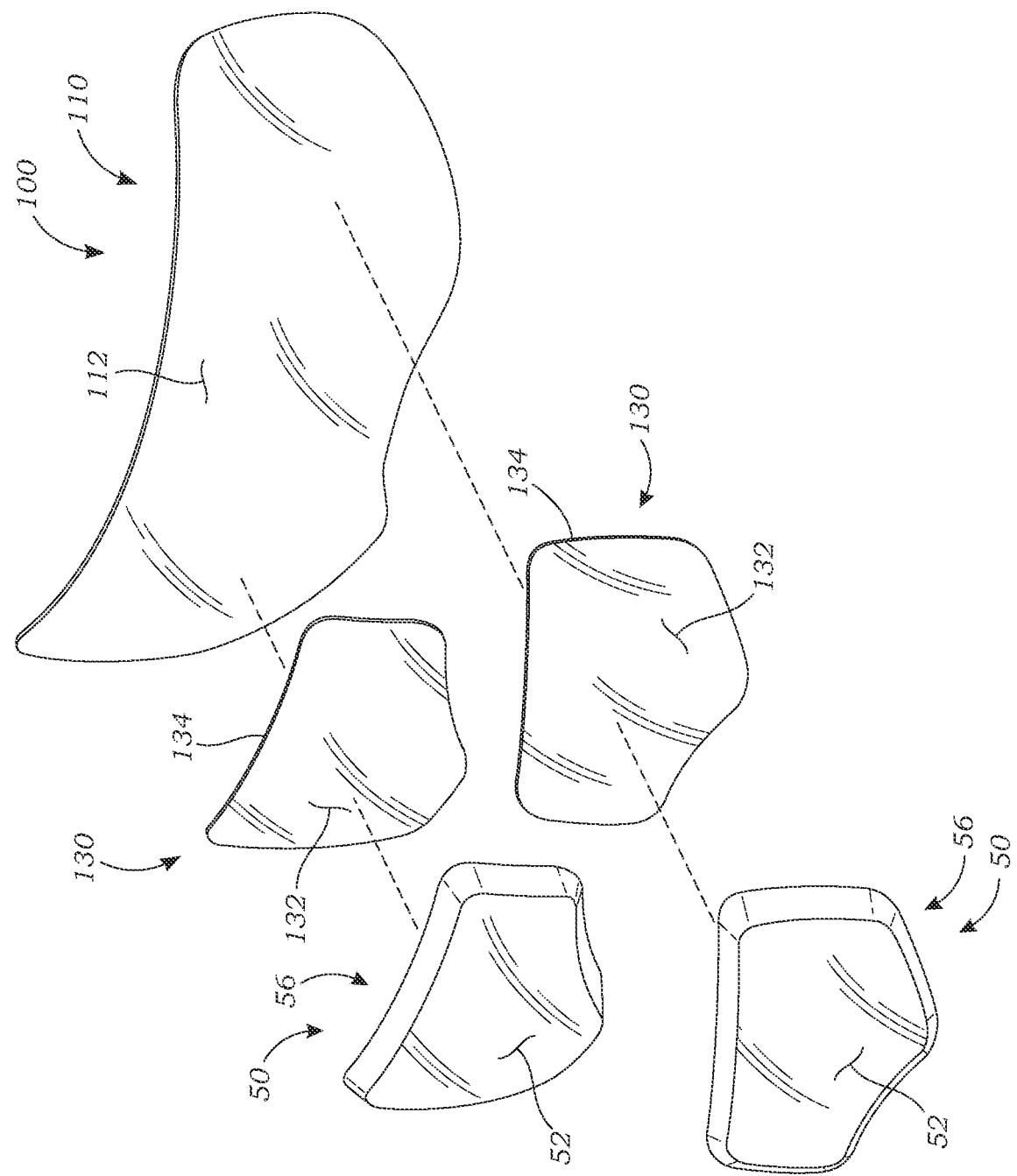
FIG. 12 is an exploded front perspective view of a further alternative exemplary embodiment thereof, in accordance with at least one embodiment.

In terms of the assembly of the prescription lenses 50 with or onto any such shield lens 90, 110, as again facilitated by the net or near-net shapes of the mating surfaces in the exemplary embodiment wherein the components are formed separately as through molding, additive manufacturing, or otherwise and are then to be joined in a subsequent operation, such assembly may be accomplished through any means now known or later developed, including but not limited to bonding, including UV light cured solvent and other agents. In an exemplary embodiment, an aggressive bonding technology is employed so as to render the resulting lens assembly or apparatus 20 substantially unitary with the lenses 50 and shield 90, 110 mechanochemically affixed, again without any compromise of the lens optics. While in the above-described exemplary embodiment all such lens components may be polycarbonate, it is also contemplated that only one such component would be polycarbonate (e.g., the shield lens) and the other component (e.g., the prescription lenses) may be another appropriate material such as nylon or urethane-based monomer, which may further facilitate bonding or assembly of such components together while again not compromising the finished assembly optics. As shown in the exploded perspective view of FIG. 12 illustrating a further alternative exemplary embodiment of a lens mount apparatus 20 according to aspects of the present invention, a relatively thin layer or laminate 130 may be applied or formed between the lenses 50 and shield 110 to facilitate assembly. Such may be a solvent material or adhesive or a UV-curable material that upon activation by UV light when the parts 50, 110 are assembled with the layer 130 therebetween serves to fuse or bond the parts together along their adjacent surfaces. Those skilled in the art will appreciate that with such parts 50, 110 formed of a clear polycarbonate, nylon, urethane, or the like, UV light can thus pass through from either and really any direction to facilitate activation of the UV-curable adhesive and thus assembly of the parts 50, 110. To the extent that the shield 90, 110 has any surface treatment, here particularly on its outer surface 92, 112, such as a mirror finish or anti-scratch hard surface coating, the laminate layer 130 or other bonding agent facilitates such attachment of the prescription lenses 50 without the need to remove or etch or otherwise treat all or part of the shield surface to which the lenses 50 will be assembled. Furthermore, in alternative embodiments, whether or not there is any such intermediate layer 130 or some other assembly technique employed, such as described below in connection with additive manufacturing or formation of the lenses 50 directly onto the shield 90, 100, the shield surface to or on which the lenses 50 are to be joined or installed may be non-destructively disturbed or modified to facilitate such assembly. It will be appreciated that any such bonding technique or agent, whether or not represented or actually configured as a layer or laminate 130, and again whether now known or later developed, may be employed in assembling prescription lenses 50 with optical shields 90, 110 according to aspects of the present invention without departing from its spirit and scope.

Figure 13:
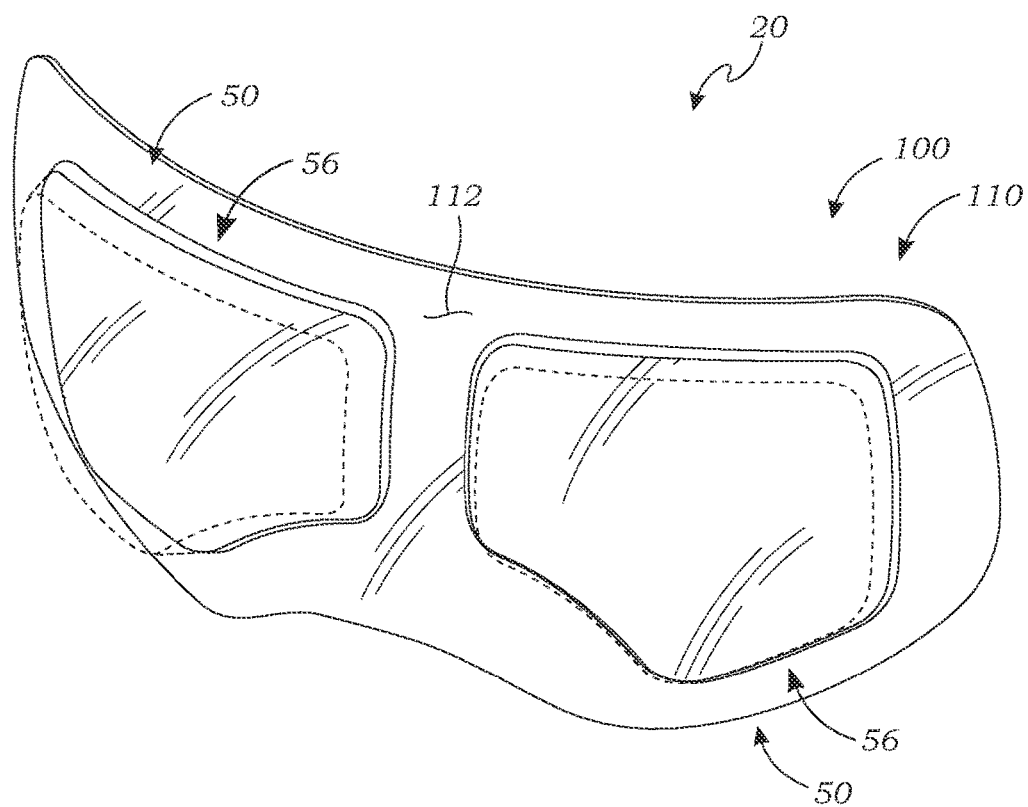
FIG. 13 is a partial front perspective view of a further alternative exemplary embodiment thereof, in accordance with at least one embodiment.

Turning next to FIG. 13, there is shown a partial perspective view of a further alternative exemplary embodiment of a lens mount assembly or apparatus 20 according to aspects of the present invention. In this exemplary embodiment, the third lens component or shield-type lens 110 (or second lens component configured as a shield or single optical lens 90) is formed first in a separate operation in a manner known in the art. But rather than molding the prescription lenses 50 directly onto the shield 110 as through compression-injection molding or separately molding the lenses 50 and then bonding or otherwise affixing them to the shield 110 in a secondary operation as in other exemplary embodiments herein, the prescription lenses 50 may be built or formed directly onto the shield 110 through an additive manufacturing process, whether now known or later developed and so including but not limited to stereolithography ("SLA"), selective laser sintering ("SLS"), vacuum deposition, and 3-D printing. It will be appreciated that in such techniques, a desired component, usually made of some kind of plastic or resin, is formed point-by-point (drop-by-drop) or layer-by-layer as by laser or light curing or depositing such plastic or resin component one slice or cross-section at a time. As such, a similar process may be employed with the shield 110 itself placed on or serving as the stage upon which the lenses 50 are formed, again, section-by section. Once more, in some embodiments, particularly if the shield 110 comprises surface treatment, such surface may be modified or disturbed before or during the deposition or formation of the lenses 50 thereon. In any case, it will be appreciated that the additive manufacturing resin laid down or applied onto the surface of the shield 110 will chemically or mechanochemically bond therewith, the layers each bonding to the one before until the entire lenses 50 are thus integrally formed on the shield 110 to complete the lens mount assembly or apparatus 20. It will be appreciated that FIG. 13 thus depicts such lens mount apparatus 20 at an intermediate stage of production with a portion but not all of the lenses 50 built, laid down, or otherwise formed on the shield lens 110. Relatedly, it will be appreciated that fundamentally, in this example, it would be the shapes of the outer surfaces 52 as laid down layer by layer that would dictate the optics or corrective properties and thus the prescriptions of the lenses 50. And by forming or building the lenses 50 or lens inserts 56 at the point of manufacture and assembly directly onto a shield 110 potentially in a "one off" process, those skilled in the art will appreciate that such a process would have the added advantage of thus forming such lenses 50 or lens inserts 56 with a specific prescription, rather than as blanks into which a desired prescription would be later cut or ground, thereby avoiding the time and expense of such a subsequent step. The result is finished solid prescription lenses 50 mechanochemically bonded to the molded shield lens component 110, in appearance much the same as the lens mount assembly or apparatus 20 shown in FIG. 9. Again, such assembly of the prescription lenses 50 can be on either surface of any such shield 110, though once more, assembly onto the outer surface 112 is illustrated. In terms of the additive manufacturing process itself, once again, any such technique now known or later developed may be employed, including but not limited to a process according to or defined by ASME Y14.46-2017. It is also contemplated that any such additive manufacturing method may be employed in constructing only a portion of a lens 50 or effectively a layer or mounting surface onto which a lens 50 may be formed or may be bonded as previously formed such as shown in connection with the alternative exemplary embodiment of FIG. 12—that is, the layers or laminates 130 positioned on the shield 110 outer surface 112 or between the shield 110 and the lenses 50 may themselves be formed via an additive manufacturing process according to aspects of the present invention, as of course may be the lenses 50 and/or the shield 110, together or separately. It will be thus appreciated by those skilled in the art that manufacturing or assembly techniques such as herein described for use in connection with the installation of prescription lenses 50 onto shield-type and other lenses 90, 110 are not mutually exclusive but may instead be combined and substituted in any appropriate manner without departing from the spirit and scope of the invention.

There is thus described herein in a number of exemplary embodiments a lens mount apparatus 20 and related method of its production that cleverly and advantageously entails permanent assembly of prescription lens blanks or finished prescription lenses onto a shield lens or some other lens support structure for use in protective or military eyewear, goggles, or other such applications. Particularly, according to one or more exemplary embodiments, such finished prescription lenses may be formed and then permanently installed or as through an additive manufacturing process be effectively built or formed directly onto an inner or outer shield lens or support structure surface in a secondary operation without compromising the optics of the prescription lenses or any shield lens, and thus without having to engage in a further secondary operation related to cutting or grinding the prescription into the lenses. Further, where the prescription lenses are formed on an outer surface of such a shield lens, or are otherwise separated from the wearer's eyes by at least one shield lens or structure, the lenses provide further protection and improved performance, such as in connection with military ballistic or other such impact testing, as by further preventing any lens components that may fail or crack from being toward or coming into contact with a wearer's eye. As such, it will be appreciated that a number of advantageous lens assemblies are herein presented and, again, that a variety of related configurations are possible according to aspects of the present invention, such that the exemplary embodiments are to be understood as illustrative and non-limiting.

Furthermore, aspects of the present invention in such eyewear or ophthalmological contexts may thus be described in at least four further exemplary embodiments as follows:

1. Prescription Lenses Formed on Front of Goggle or Shield Lens. The prescription lens components shall be created and bonded in microscopic droplets of a UV-curable plastic monomer deposited and cured with UV light all controlled by computer on an additive manufacturing methodology machine. The result of the UV-cured plastic monomer shall be finished solid prescription lenses attached and bonded to the front (exterior) surface of the molded goggle or shield lens component. Prior to the process of forming the prescription lens components, the target surface area of the molded lens component to receive the prescription lens components shall be disturbed or modified to enable bonding to take place.

2. Prescription Lenses Formed on Back of Goggle or Shield Lens. The prescription lens components shall be created and bonded in microscopic droplets of a UV-curable plastic monomer deposited and cured with UV light all controlled by computer on an additive manufacturing methodology machine. The result of the UV-cured plastic monomer shall be finished solid prescription lenses attached and bonded to the back (interior) surface of the molded goggle or shield lens component. Prior to the process of forming the prescription lens components, the target surface area of the molded lens component to receive the prescription lens components shall be disturbed or modified to enable bonding to take place.

3. Prescription Lenses Affixed on Front of Goggle or Shield Lens. The prescription lens components shall be created using existing optical lens manufacturing technology for creating prescription lenses. The concave curvature of back (interior) surface of the prescription lens components shall be made to match the convex curvature of the front (exterior) surface of the molded goggle or shield lens component. Using aggressive bonding technology, the prescription lens components shall be bonded to the front surface of the molded goggle or shield lens component. Prior to the process, the target surface area of the molded goggle or shield lens component to receive the prescription lens components shall be disturbed or modified to enable bonding to take place.

4. Prescription Lenses Affixed on Back of Goggle or Shield Lens. The prescription lens components shall be created using existing optical lens manufacturing technology for creating prescription lenses. The convex curvature of front (exterior) surface of the prescription lens components shall be made to match the concave curvature of the back (interior) surface of the molded goggle or shield lens component. Using aggressive bonding technology, the prescription lens components shall be bonded to the back surface of the molded goggle or shield lens component. Prior to the process, the target surface area of the molded goggle or shield lens component to receive the prescription lens components shall be disturbed or modified to enable bonding to take place.

Once again, other such processes or combinations or hybrids thereof may be employed in forming a lens assembly or lens mount apparatus 20 according to aspects of the present invention without departing from its spirit and scope, such that the described examples are to be understood as illustrative and non-limiting.

By way of further illustration and not limitation, prescription lenses 50 or inserts 56 as defining a first lens component 30 may be formed integrally with a second lens support device 70 or second optical lens 90 defining a second lens component 60 in any manner consistent with or according to aspects of the present invention so as to form an integral or unibody lens assembly or lens mount apparatus 20 as herein disclosed. Moreover, as also herein disclosed, such lens components 30, 60, and in particular exemplary embodiments a second lens support device 70 on which the prescription lenses 50 defining the first lens component 30 are installed, which second lens support device 70 may again also entail or define a second optical lens 90, may be further formed having at least one mechanical attachment feature 76 integral with such second lens support device 70. While in the exemplary goggle context of FIGS. 4-8 such second mechanical attachment feature 76 is shown and described as being in the form of a lens perimeter flange 82, which may itself be formed with further attachment features such as notches or holes as required or desired so as to engage with other eyewear (e.g., shield or goggle) structure in assembling the lens mount apparatus 20 therewith, it will again be appreciated that any such structure now known or later developed as appropriate for a particular context, including but not limited to a hole or cross-hole, walls and sloped surfaces, a bracket, a notch, keyed surfaces, and a toothed surface, may be employed according to aspects of the present invention without departing from its spirit and scope, such that the exemplary embodiments are to be understood as merely illustrative and non-limiting. By way of still further illustration and not limitation, a lens mount apparatus 20 according to aspects of the present invention may thus be configured so as to removably engage a hole, slot, or other feature in a shield or goggle assembly so as to replace a universal prescription lens carrier ("UPLC") configured for such installation such as manufactured and sold by Revision Eyewear, Inc. and/or Revision Military Inc. in Montreal, Canada (collectively, "Revision"), including but not limited to such "Protective Eyewear Including Auxiliary Lenses" as shown and described in the above-referenced U.S. Pat. No. 7,641,333 to Revision, whereby a lens mount apparatus 20 according to aspects of the present invention effectively forms or defines a replacement or universal or unibody UPLC addressing shortcomings of and as an improvement over the Revision UPLC as, for example, by having integrated, relatively larger prescription lenses rather than size-constrained lenses that must be separately formed and assembled within (or popped into and out of) the Revision UPLC. Accordingly, any such lens mount apparatus 20 may once more be formed with any appropriate mechanical attachment features, whether as a boss, tab, or keyed feature for engagement with a shield frame or legs for engagement with a goggle frame or otherwise. These and other embodiments and related advantages of a lens mount apparatus 20 according to aspects of the present invention will be appreciated by those skilled in the art, such that the exemplary embodiments shown and described herein are to again be understood as illustrative and non-limiting.

Figures 14, 15:
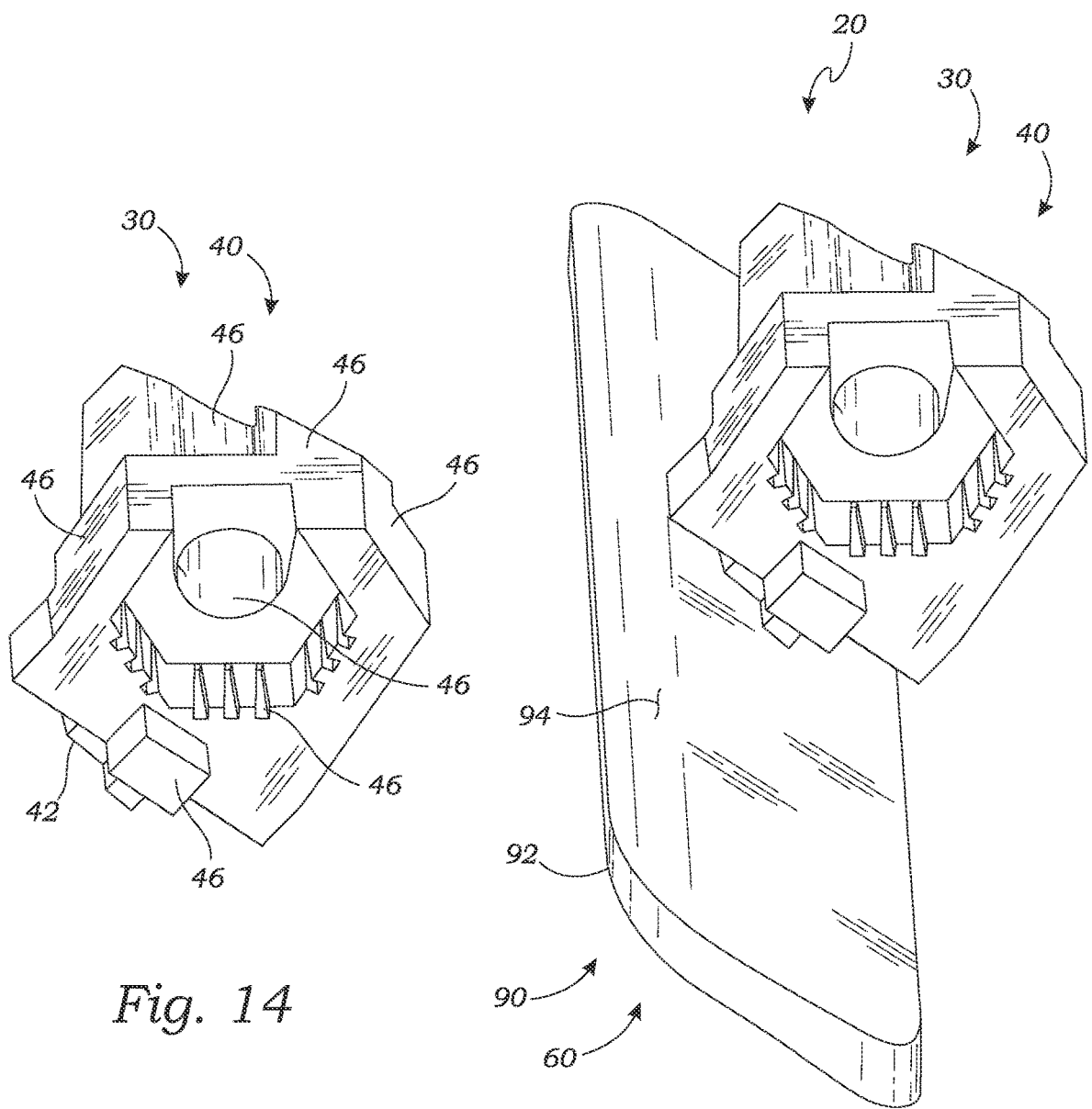
FIG. 14 is a perspective view of a still further alternative exemplary first lens component, in accordance with at least one embodiment.
FIG. 15 is a perspective view of an alternative lens mount apparatus incorporating the first lens component of FIG. 14, in accordance with at least one embodiment.

Finally, turning to FIGS. 14 and 15, there are shown perspective views of yet another alternative lens mount apparatus 20 and first and second lens components 30, 60 thereof according to aspects of the present invention. Once more, in this further exemplary embodiment, the first lens component 30 configured as a lens support device 40 is formed first as through an injection molding process. Here, the lens support device 40 is formed having a number of mechanical attachment features 46, including a cross-hole, walls and sloped surfaces, a bracket, a notch, keyed surfaces, and a toothed surface here positioned somewhat circumferentially about the cross-hole. It will be appreciated that all such features 46, alone or in various combinations, may cooperate to later mount the lens support device 40 to other structure as part of a larger assembly and that certain features serve more of a fastening purpose and certain other features more of a location or positioning purpose—any such mechanical fastening features now known or later developed may be incorporated in any such lens support device 40. Here, it will be appreciated that all such features may be formed via injection molding but that even so by having certain regions of greater thickness and a number of "corners" and therefore potential stress points in the material, there is the possibility that stresses, distortions, or other defects might be induced within the part, such that it is again desirable to not also mold any optical lens feature in one "shot" with the lens support device 40 whereby such defects may be found in the optical lens as well. Accordingly, with reference to FIG. 15, there is shown a completed lens mount apparatus 20 wherein the second lens component 60 here configured as a substantially rectangular optical lens 90 is attached or formed integrally with the first lens component 30 configured as the lens support device 40 as through a subsequent compression-injection molding process. In essence, the lens support device 40, once formed, may either remain in the same mold cavity or be transferred to a different mold or cavity and either way be held in a fixed position as the optical lens 90 is molded such that the rear or inner surface 94 of the lens 90 is affixed or fused to the front or outer surface 42 (FIG. 14) of the lens support device 40 in the arrangement of the lens mount apparatus 20 shown in FIG. 15. While the lens 90 is shown as having a particular rectangular profile and thickness and with the lens support device 40 substantially centered thereon, it will again be appreciated that a virtually infinite variety of configurations of the lens 90 and lens support device 40 and their engagement are possible without departing from the spirit and scope of the present invention.

Aspects of the present specification may also be described as follows:

1. A lens mount apparatus comprising a first lens component and a second lens component formed integrally with the first lens component, resulting in mechanochemical attachment of the second lens component with the first lens component to produce the unitary lens mount apparatus without compromising the lens mount apparatus optics, wherein at least one of the first and second lens components is an optical lens.

2. The apparatus of embodiment 1 wherein the first lens component is a lens support device and the second lens component is an optical lens.

3. The apparatus of embodiment 2 wherein the lens support device is formed as a structural member having at least one mechanical attachment feature.

4. The apparatus of embodiment 3 wherein the at least one mechanical attachment feature is selected from the group consisting of a hole, a wall, a bracket, a key, a keyway, a notch, a sloped surface, and a toothed surface.

5. The apparatus of embodiment 1 wherein the first lens component is a first optical lens and the second lens component is a lens support device.

6. The apparatus of embodiment 5 wherein the lens support device is formed as a structural member having at least one mechanical attachment feature.

7. The apparatus of embodiment 6 wherein the at least one mechanical attachment feature is selected from the group consisting of a hole, a wall, a bracket, a key, a keyway, a notch, a sloped surface, and a toothed surface.

8. The apparatus of any of embodiments 5-7 wherein the second lens component is simultaneously a second optical lens, the first and second optical lenses together defining the lens mount apparatus optics.

9. The apparatus of embodiment 8 wherein the first lens component comprises two spaced-apart lens inserts.

10. The apparatus of embodiment 9 wherein each lens insert is configured for being formed as a finished prescription lens in a secondary operation.

11. The apparatus of embodiment 9 wherein each lens insert is formed as a finished prescription lens prior to assembly of the first lens component with the second lens component.

12. The apparatus of embodiment 9 wherein each lens insert is formed as a finished prescription lens during assembly of the first lens component with the second lens component.

13. The apparatus of any of embodiments 9-12 wherein each lens insert is formed through additive manufacturing.

14. The apparatus of embodiment 13 wherein each lens insert is formed as a finished prescription lens directly onto the second lens component.

15. The apparatus of any of embodiments 9-12 wherein each lens insert is molded.

16. The apparatus of embodiment 15 wherein each lens insert is formed as a finished prescription lens prior to assembly onto the second lens component.

17. The apparatus of embodiment 15 wherein each lens insert is formed as prescription lens blank configured for becoming a finished prescription lens in a secondary operation.

18. The apparatus of any of embodiments 13 and 15-17 wherein a first curvature of each lens insert of the first lens component corresponds to a second curvature of the second lens component for surface-to-surface contact during assembly.

19. The apparatus of any of embodiments 5-18 wherein the second lens component is a shield.

20. The apparatus of any of embodiments 2-19 wherein the lens support device comprises a continuous lens wall defining a lens wall perimeter and a perimeter flange extending substantially inwardly from at least a portion of the lens wall perimeter, the perimeter flange comprising at least one mechanical attachment feature.

21. The apparatus of embodiment 20 wherein the at least one mechanical attachment feature is selected from the group consisting of a hole, a wall, a bracket, a key, a keyway, a notch, a sloped surface, and a toothed surface.

22. The apparatus of embodiment 20 or embodiment 21 wherein the perimeter flange further extends substantially outwardly from at least a portion of the lens wall perimeter so as to define an outwardly-facing perimeter flange surface offset from the lens wall, and a third lens component defining an outer third optical lens is positioned adjacent to the perimeter flange surface so as to form an air gap between the third optical lens and the lens wall of the lens support device.

23. The apparatus of embodiment 22 further comprising an adhesive open-cell foam gasket positioned between the perimeter flange surface and the outer optical lens and thereby attaching the outer optical lens to the lens support device and forming a relatively larger air gap therebetween.

24. The apparatus of any of embodiments 2-23 wherein the lens support device is a shield.

25. The apparatus of any of embodiments 1-24 wherein the first lens component is on a second lens component outer surface.

26. The apparatus of any of embodiments 1-24 wherein the first lens component is on a second lens component inner surface.

27. The apparatus of any of embodiments 1-26 wherein a laminate is positioned between the first and second lens components to facilitate assembly.

28. The apparatus of embodiment 27 wherein the laminate is formed through additive manufacturing.

29. The apparatus of embodiment 27 or embodiment 28 wherein the laminate is UV light curable.

30. The apparatus of any of embodiments 1-29 wherein the first lens component defines a first perimeter and the second lens component defines a second perimeter, the second perimeter being greater than or equal to the first perimeter.

31. The apparatus of any of embodiments 1-30 wherein the first lens component is formed from a first material and the second lens component is formed from a second material, the first and second materials being the same.

32. The apparatus of any of embodiments 1-30 wherein the first lens component is formed from a first material and the second lens component is formed from a second material, the first and second materials being different.

33. The apparatus of any of embodiments 1-32 wherein the optical lens has a reflective optical surface so as to form a mirror.

34. The apparatus of any of embodiments 1-33 wherein the second lens component has a surface treatment.

35. The apparatus of embodiment 34 wherein the surface treatment is disturbed prior to assembly of the first lens component with the second lens component.

36. A lens mount apparatus comprising a first lens component comprising two spaced-apart lens inserts together forming a first optical lens and a second lens component comprising a second optical lens defining a continuous outer lens wall having an inner surface and further comprising a lens support device, the second lens component formed integrally with the first lens component, resulting in mechanochemical attachment of the second lens component with the first lens component to produce the unitary lens mount apparatus without compromising the lens mount apparatus optics, wherein the lens inserts are fused to the lens wall, the resulting first and second optical lenses together defining the lens mount apparatus optics.

37. A lens mount apparatus comprising a first lens component comprising two spaced-apart lens inserts together defining a first optical lens, a second lens component defining a second optical lens and a lens support device, and a third lens component defining a third optical lens installed spaced from the second lens component, the lens inserts of the first lens component formed integrally with the third lens component.

38. A method of assembling a lens mount apparatus comprising the steps of forming a first lens component and joining a second lens component with the first lens component, resulting in mechanochemical attachment of the second lens component with the first lens component to produce the unitary lens mount apparatus without compromising the lens mount apparatus optics, wherein at least one of the first and second lens components is an optical lens.

39. The method of embodiment 38 wherein the step of forming the first lens component comprises molding the first lens component as a pair of lens inserts.

40. The method of embodiment 39 comprising the further step of forming a prescription in each lens insert before assembly with the second lens component.

41. The method of embodiment 39 comprising the further step of forming a prescription in each lens insert after assembly with the second lens component.

42. The method of embodiment 39 comprising the further step of forming a prescription in each lens insert during assembly with the second lens component.

43. The method of any of embodiments 39-42 wherein the step of joining the second lens component with the first lens component comprises bonding the lens inserts onto the second lens component.

44. The method of embodiment 38 wherein the step of forming the first lens component comprises building the first lens component as a pair of lens inserts directly onto the second lens component through additive manufacturing, whereby the step of joining the second lens component with the first lens component is concurrent with the step of forming the first lens component.

45. The method of embodiment 44 wherein the step of building the first lens component comprises forming a prescription in each lens insert during assembly with the second lens component.

46. The method of any of embodiments 38-45 wherein the first lens component is joined to an outer surface of the second lens component.

47. The method of any of embodiments 38-45 wherein the first lens component is joined to an inner surface of the second lens component.

48. The method of any of embodiments 38-47 further comprising placing a laminate between the first lens component and the second lens component.

49. The method of embodiment 48 wherein the laminate is applied through additive manufacturing.

50. The method of embodiment 49 wherein the laminate is UV light curable.

51. The method of any of embodiments 38-50 further comprising molding the second lens component as a shield.

52. The method of any of embodiments 38-51 wherein the second lens component comprises a lens support device having at least one mechanical attachment feature.

53. The method of any of embodiments 38-52 further comprising disturbing a surface treatment of the second lens component prior to assembly of the first lens component with the second lens component.

In closing, it is to be understood that although aspects of the present specification are highlighted by referring to specific embodiments, one skilled in the art will readily appreciate that these disclosed embodiments are only illustrative of the principles of the subject matter disclosed herein. Because the principles of the specification may be practiced in a number of configurations beyond those shown and described, it is to be understood that the specification is not in any way limited by the exemplary embodiments, but is generally directed to a lens mount apparatus and is able to take numerous forms to do so without departing from the spirit of the specification. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present specification, which is defined solely by the claims. It will also be appreciated by those skilled in the art that the present specification is not limited to the particular geometries and materials of construction disclosed, but may instead entail other functionally comparable structures or materials, now known or later developed, without departing from the spirit of the specification. Accordingly, the present specification is not limited to that precisely as shown and described.

Certain embodiments of the present invention are described herein, including the best mode known to the inventor(s) for carrying out the invention. Of course, variations on these described embodiments will become apparent to those of ordinary skill in the art upon reading the foregoing description. The inventor(s) expect skilled artisans to employ such variations as appropriate, and the inventor(s) intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. A lens mount apparatus comprising:
   a first lens component comprising two spaced-apart lens inserts together defining a first optical lens; and
   a second lens component defining a second optical lens having an inner surface and an opposite outer surface and further defining a lens support device comprising a structural member having at least one mechanical attachment feature, the first lens component joined integrally and permanently with the second lens component to produce the unitary, one-piece lens mount apparatus comprising the first and second lens components without compromising the lens mount apparatus optics, wherein the lens inserts are fused to one of the inner surface and the outer surface of the second optical lens such that the first optical lens and the second optical lens are incapable of nondestructive separation and the resulting first and second optical lenses together define the lens mount apparatus optics.

2. The apparatus of claim 1 wherein each lens insert is configured as a finished prescription lens.

3. The apparatus of claim 1 wherein each lens insert is configured for being formed as a finished prescription lens in a secondary operation.

4. The apparatus of claim 1 wherein each lens insert is formed through additive manufacturing as a finished prescription lens directly onto the second lens component.

5. The apparatus of claim 1 wherein the first lens component is formed on the inner surface of the second lens component.

6. The apparatus of claim 1 wherein the at least one mechanical attachment feature is selected from the group consisting of a hole, a cross-hole, a boss, a tab, a leg, a bracket, a key, a keyway, a notch, a toothed surface, and a wall or a sloped surface at an angle to the optical lens.

7. The apparatus of claim 1 wherein the structural member is formed on the outer surface of the second lens component.

8. The apparatus of claim 7 wherein the structural member is formed through additive manufacturing directly onto the second lens component.

9. The apparatus of claim 1 wherein the first lens component is formed from a first material and the second lens component is formed from a second material, the first and second materials being the same.

10. The apparatus of claim 1 wherein the first lens component is formed from a first material and the second lens component is formed from a second material, the first and second materials being different.

11. A lens mount apparatus comprising:
a first lens component comprising two spaced-apart lens inserts together defining a first optical lens; and
a second lens component defining a second optical lens formed as a shield, wherein each lens insert and the shield are together formed through additive manufacturing as comprising finished prescription lenses defining the first optical lens formed directly onto the shield defining the second optical lens to produce the unitary, one-piece lens mount apparatus comprising the first and second lens components without compromising the lens mount apparatus optics, wherein the lens inserts are integral with the shield such that the first optical lens and the second optical lens are incapable of nondestructive separation and the resulting first and second optical lenses together define the lens mount apparatus optics.

12. The apparatus of claim 11 wherein:
the shield comprises a continuous outer lens wall having an outer surface and an opposite inner surface; and
the lens inserts are formed on the inner surface of the outer lens wall.

13. The apparatus of claim 12 wherein the outer surface is convex and the inner surface is concave.

14. The apparatus of claim 11 wherein the second lens component is simultaneously a lens support device comprising a structural member having at least one mechanical attachment feature.

15. The apparatus of claim 14 wherein the at least one mechanical attachment feature is selected from the group consisting of a hole, a cross-hole, a boss, a tab, a leg, a bracket, a key, a keyway, a notch, a toothed surface, and a wall or a sloped surface at an angle to the optical lens.

16. The apparatus of claim 14 wherein the structural member is formed on the outer surface of the second lens component.

17. The apparatus of claim 16 wherein the structural member is formed through additive manufacturing directly onto the second lens component.

18. The apparatus of claim 11 wherein the first lens component is formed from a first material and the second lens component is formed from a second material, the first and second materials being the same.

19. The apparatus of claim 11 wherein the first lens component is formed from a first material and the second lens component is formed from a second material, the first and second materials being different.

20. A lens mount apparatus comprising:
a first lens component comprising two spaced-apart lens inserts each configured as a finished prescription lens and together defining a first optical lens; and
a second lens component defining a lens support device comprising a structural member having at least one mechanical attachment feature, the lens support device formed so as to extend forwardly of the first lens component, the first lens component joined integrally and permanently with the second lens component to produce the unitary, one-piece lens mount apparatus comprising the first and second lens components without compromising the lens mount apparatus optics, wherein the lens inserts are integral with the lens support device such that the first lens component and the second lens component are incapable of nondestructive separation.

* * * * *